(12) United States Patent
Afzali-Ardakani et al.

(10) Patent No.: US 9,766,229 B2
(45) Date of Patent: Sep. 19, 2017

(54) GRAPHENE NANOMESH BASED CHARGE SENSOR

(71) Applicants: International Business Machines Corporation, Armonk, NY (US); Egypt Nanotechnologies Center (EGNC), Cairo-Alexandria Desert Road (EG)

(72) Inventors: Ali Afzali-Ardakani, Ossining, NY (US); Shu-jen Han, Cortlandt Manor, NY (US); Amal Kasry, White Plains, NY (US); Ahmed Maarouf, Mohegan Lake, NY (US); Glenn J. Martyna, Croton on Hudson, NY (US); Razvan Nistor, New York, NY (US); Hsinyu Tsai, White Plains, NY (US)

(73) Assignees: International Business Machines Corporation, Armonko, NY (US); Egypt Nanotechnology Center, Cairo (EG)

( * ) Notice: Subject to any disclaimer, the term of this patent is extended or adjusted under 35 U.S.C. 154(b) by 11 days.

(21) Appl. No.: 14/699,318

(22) Filed: Apr. 29, 2015

(65) Prior Publication Data
US 2015/0276726 A1    Oct. 1, 2015

Related U.S. Application Data

(62) Division of application No. 13/310,194, filed on Dec. 2, 2011, now Pat. No. 9,102,540.

(51) Int. Cl.
| | |
|---|---|
| B82Y 30/00 | (2011.01) |
| C01B 31/04 | (2006.01) |
| C40B 60/10 | (2006.01) |
| G01N 33/543 | (2006.01) |
| G01N 33/551 | (2006.01) |
| G01N 33/53 | (2006.01) |
| B82Y 40/00 | (2011.01) |

(52) U.S. Cl.
CPC .......... *G01N 33/5308* (2013.01); *B82Y 30/00* (2013.01); *B82Y 40/00* (2013.01); *C01B 31/0484* (2013.01); *G01N 33/54373* (2013.01); *G01N 33/54393* (2013.01); *G01N 33/551* (2013.01); *G01N 2400/00* (2013.01)

(58) Field of Classification Search
CPC ....................................................... G01N 33/53
See application file for complete search history.

(56) References Cited

U.S. PATENT DOCUMENTS

| 2005/0265914 A1* | 12/2005 | Gu | .................. B82Y 15/00 423/445 B |
| --- | --- | --- | --- |
| 2008/0257015 A1 | 10/2008 | Lukehart et al. | |
| 2010/0105834 A1 | 4/2010 | Tour | |
| 2010/0143198 A1 | 6/2010 | Damiano et al. | |
| 2010/0218801 A1 | 9/2010 | Song et al. | |
| 2011/0201201 A1* | 8/2011 | Arnold | ................... B82Y 30/00 438/694 |
| 2011/0237000 A1 | 9/2011 | Tey et al. | |
| 2011/0257033 A1 | 10/2011 | Strano et al. | |
| 2011/0274928 A1* | 11/2011 | Liu | ......................... B82Y 25/00 428/402 |
| 2012/0301953 A1* | 11/2012 | Duan | ..................... B82Y 30/00 435/287.9 |
| 2013/0131383 A1 | 5/2013 | Afzali-Ardakani et al. | |

FOREIGN PATENT DOCUMENTS

| WO | 2009158117 | 12/2009 |
|---|---|---|
| WO | 2010036210 | 4/2010 |
| WO | 2010144157 | 12/2010 |
| WO | 2011011828 | 2/2011 |
| WO | 2011094597 A2 | 8/2011 |

OTHER PUBLICATIONS

Chen et al., Charged Impurity Scattering in Graphene, Nature Physics, vol. 4, 2008, pp. 377-381.
Bai et al., Graphene Nanomesh, Nature Nanotechnology, vol. 5, 2010, pp. 190-194.
Pedersen et al., Graphene Antidot Lattices: Designed Defects and Spin Qubits, Phys. Rev. Lett., vol. 100, 2008, 136804, 4 pages.
Boukhvalov et al., Tuning the Gap in Bilayer Graphene Using Chemical Functionalization: Density Functional Calculations, Phys. Rev. B, vol. 78, 2008, 085413, 5 pages.
Alwarappan et al., Enzyme-Doped Graphene Nanosheets for Enhanced Glucose Biosensing, J. Phys. Chem. C, vol. 114, 2010, pp. 12920-12924.
Wang et al., Nitrogen-Doped Graphene and its Application in Electrochemical Biosensing, ACS Nano, vol. 4, 2010, pp. 1790-1798.

(Continued)

*Primary Examiner* — Amy M Bunker
(74) *Attorney, Agent, or Firm* — Ryan, Mason & Lewis, LLP (57) ABSTRACT

A graphene nanomesh based charge sensor and method for producing a graphene nanomesh based charge sensor. A graphene nanomesh based charge sensor includes a graphene nanomesh with a patterned array of multiple holes created by generating multiple holes in graphene in a periodic way, wherein: an edge of each of the multiple holes of the graphene nanomesh is passivated; and the passivated edge of each of the multiple holes of the graphene nanomesh is functionalized with a chemical compound that facilitates chemical binding of a receptor of a target molecule to the edge of one or more of the multiple holes, allowing the target molecule to bind to the receptor, causing a charge to be transferred to the graphene nanomesh to produce a graphene nanomesh based charge sensor for the target molecule.

5 Claims, 5 Drawing Sheets

(56) References Cited

OTHER PUBLICATIONS

Li et al., Development of Boronic Acid Grafted Random Copolymer Sensing Fluid for Continuous Glucose Monitoring, Biomacromolecules, vol. 10, 2009, pp. 113-118.
Nishiyabu et al., Boronic Acid Building Blocks: Tools for Sensing and Separation, Chem. Commun., 2010, 1-18.
Boukhvalov et al. Tuning the Gap in Bilayer Graphene Using Chemical Functionalization: Density Functional Calculations, Physical Review B, 2008, 78, 1-5.
Bai et al. Graphene Nanomesh, Nature Technology Letters, 2010, 5, 190-194.
Sahin et al. Graphene Nanomeshes: Existence of Defect-Induced Dirac Fermions on Graphene Host Matrix, Cond-Mat.Mes-Hall, 2011, 1-8.

* cited by examiner

GRAPHENE NANOMESH BASED CHARGE SENSOR

CROSS-REFERENCE TO RELATED APPLICATIONS

This application is a continuation of U.S. patent application Ser. No. 13/310,194 (now U.S. Pat. No. 9,102,540), filed Dec. 2, 2011, and incorporated by reference herein.

Also, the present application is related to U.S. patent application entitled "Doped, Passivated Graphene Nanomesh, Method of Making the Doped, Passivated Graphene Nanomesh, and Semiconductor Device Including the Doped, Passivated Graphene Nanomesh," identified as Ser. No. 13/194,976, and filed on Jul. 31, 2011, which is incorporated by reference herein.

FIELD OF THE INVENTION

Embodiments of the invention generally relate to electronic devices and, more particularly, to charge sensors.

BACKGROUND OF THE INVENTION

The efficiency of biosensors can depend, for example, on a biosensor's limit of detection as well as a biosensor's properties. Low limits of detection are needed for cases of very small target molecules or very low target concentrations. Non-specific binding can lead to false detection. Accordingly, there is a need for a functionalized graphene nanomesh (GNM) system that provides a low limit of detection and a high resistance to non-specific binding.

SUMMARY OF THE INVENTION

In one aspect of the invention, a method for producing a graphene nanomesh based charge sensor is provided. The method includes the steps of generating multiple holes in graphene in a periodic way to create a graphene nanomesh with a patterned array of multiple holes, passivating an edge of each of the multiple holes of the graphene nanomesh to allow for functionalization of the graphene nanomesh, and functionalizing the passivated edge of each of the multiple holes of the graphene nanomesh with a chemical compound that facilitates chemical binding of a receptor of a target molecule to the edge of one or more of the multiple holes, allowing the target molecule to bind to the receptor, causing a charge to be transferred to the graphene nanomesh to produce a graphene nanomesh based charge sensor for the target molecule.

Another aspect of the invention includes a graphene nanomesh based charge sensor, which includes a graphene nanomesh with a patterned array of multiple holes created by generating multiple holes in graphene in a periodic way, wherein an edge of each of the multiple holes of the graphene nanomesh is passivated, and the passivated edge of each of the multiple holes of the graphene nanomesh is functionalized with a chemical compound that facilitates chemical binding of a receptor of a target molecule to the edge of one or more of the multiple holes, allowing the target molecule to bind to the receptor, causing a charge to be transferred to the graphene nanomesh to produce a graphene nanomesh based charge sensor for the target molecule.

These and other objects, features and advantages of the present invention will become apparent from the following detailed description of illustrative embodiments thereof, which is to be read in connection with the accompanying drawings.

DETAILED DESCRIPTION OF EMBODIMENTS

An aspect of the invention includes a graphene nanomesh based charge sensor. As detailed herein, for example, in accordance with an embodiment of the invention, a molecule (for example, boronic acid) binds to graphene, wherein there is charge transfer. Also, an aspect of the invention combines the ability to dope graphene and change conductivity with selective chemistry for sensing. Accordingly, at least one embodiment of the invention can be implemented as a sensor.

As described herein, an aspect of the invention includes creating a graphene nanomesh based system whose resistance sensitivity depends on the charge transferred thereto. Such a system includes a graphene nanomesh (GNM), a receptor, and a target molecule. According to an embodiment of the invention, an example of a target molecule is glucose, and an example of the receptor is boronic acid. In general, the receptor is chosen so as to cause a charge transfer to the GNM upon the binding between the receptor and the target molecule.

Graphene nanomeshes are carbon based structures that can be generated, for example, by creating holes in a graphene sheet in a periodic way. For example, a triangular lattice of 20 nm holes can be created in a graphene sheet. Hole size can be smaller or larger, depending on the application at hand. Three geometrical parameters characterize a GNM: hole lattice, hole size, and lattice constant. Depending on these parameters, the GNM may be intrinsically semiconducting with a non-zero gap (unlike graphene that has a zero gap with a vanishing density of states (DOS)), or quasi-metallic like graphene, with a vanishing DOS at the Fermi energy.

The creation of the holes leaves active carbon sites at the rims of the holes. By selective passivation of these holes, one can control the termination of the carbon dangling bonds can be controlled, leading, in some cases, to the doping of the graphene sheet. As an example, the holes can be created in a water vapor (or air) environment, leading to the passivation of the holes with H, O or OH groups. Another example can include creating the holes in an ammonia atmosphere, where the holes are passivated with H an NH2 groups.

An aspect of the invention includes using a graphene nanomesh that has been passivated and functionalized in such a way to bind to certain molecular species. As an example, a graphene nanomesh created in air is suitable for use in binding a receptor such as boronic acid, for targeting glucose molecules. By way of example, an embodiment of the invention can include using a graphene nanomesh where regions of the graphene sheet are removed, the edges are selectively passivated, and specific receptor molecules bind to the edges of the holes of the formed nanomesh.

As detailed herein, for example, holes can be created in a graphene sheet in air, which leads to the passivation of the carbon dangling bonds in the edges of the holes with oxygen or hydrogen or an OH group. For each target molecule required, a receptor molecule is chosen such that it would chemically bind to the target molecule, irrespective of the size of the target molecule. Chemical treatment follows to bind the needed receptor molecule to the edges of the passivated holes. In addition, as described herein, an aspect of the invention includes a sensing mechanism that uses an electronic method based on a charge transfer mechanism.

Accordingly, an aspect of the invention includes a high sensitivity sensor. The detection techniques are based on the change in the sheet conductance of the GNM upon a charge transfer event. The electronic properties of the (now doped) GNM are such that the charges are delocalized. Target molecules binding to only a fraction of the receptor sites result in a proportional change in the sheet conductance.

Additionally, an aspect of the invention includes control of the density of the receptor sites. This is achieved by controlling the characteristics of the hole lattice (hole size and lattice constant) by determining the size and pattern of the holes. An aspect of the invention further includes providing sensor stability, wherein the receptor molecules are chemically bound to the GNM. Different passivations of the GNM can be achieved (for example, O, OH, NH2, etc.), permitting various receptors to chemically bind to the passivated hole edges, leading to a stable GNM-receptor structure. A sensor such as detailed in accordance with an embodiment of the invention can be used in a wide range of applications, such as, for example, biosensors, chemical sensors, gas sensors and explosive sensors. As described herein, each sensor uses a receptor that attaches to the edges of the GNM. The receptor is chosen so as to "hunt" or seek out a specific target. The target can be, for example, the molecule of a protein, a chemical compound, a gas, or a signature of a chosen material.

By way of illustration, an embodiment of the invention can be implemented as follows. A GNM is created with a size appropriate to the receptor molecule (for example 5-20 nanometers (nm) and a 4× pitch). The holes are created, for example, using electron beam techniques or via plasma etching. The GNM is passivated so as to allow for the chemistry detailed in the subsequent step, by creating it in air, ammonia, or an environment suitable for the receptor. The receptor is a molecule that reacts with the GNM yielding a functionalized GNM. As detailed herein, the receptor is determined according to the target molecule. Also, the target molecule reacts with the receptor part of the functionalized GNM leading to a charge transfer. The charge transfer results in a boost in the conductance of the GNM.

Additionally, as an illustrative example, an embodiment of the invention can be implemented as a glucose sensor. In such an embodiment, the target molecule is glucose and the receptor is boronic acid. The reaction between the glucose and the boronic acid leads to a net charge transfer to the GNM, thereby n-doping the GNM. In this example, the glucose reacts naturally with the boronic acid. The role of the GNM is to act as a support for the receptor, and as a means for detecting the charge that is transferred to the receptor (hence the GNM) upon the chemical reaction.

Figure 1:
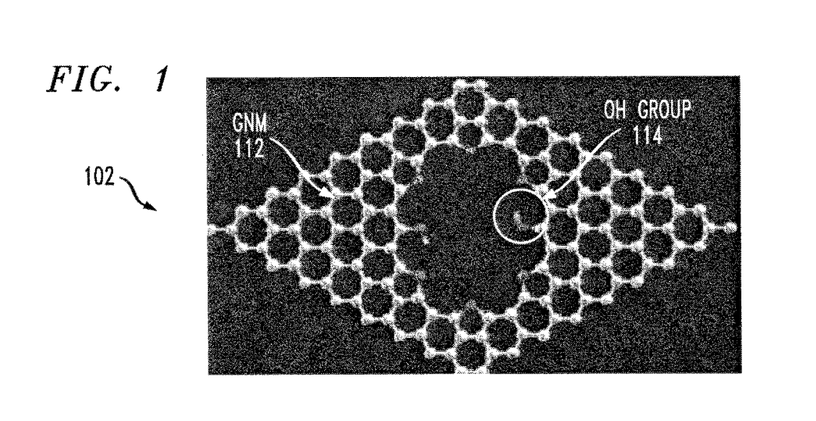
FIG. 1 is a diagram illustrating an example graphene nanomesh, according to an embodiment of the present invention.

FIG. 1 is a diagram illustrating an example graphene nanomesh structure 102, according to an embodiment of the present invention. By way of illustration, in the graphene nanomesh depiction of FIG. 1, the structure assumes that the graphene nanomesh was passivated by exposure to air. Additionally, FIG. 1 depicts the GNM 112 as well as the OH group 114.

Figure 2:
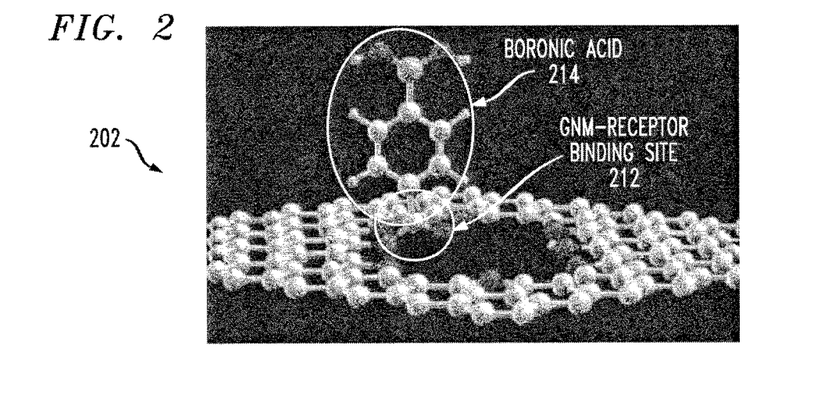
FIG. 2 is a diagram illustrating an example graphene nanomesh, according to an embodiment of the present invention.

FIG. 2 is a diagram illustrating an example graphene nanomesh 202, according to an embodiment of the present invention. By way of illustration, the graphene nanomesh depicted in FIG. 2 is a graphene nanomesh after binding to boronic acid. Additionally, FIG. 2 depicts the GNM-receptor binding site 212 as well as boronic acid 214.

Figure 3:
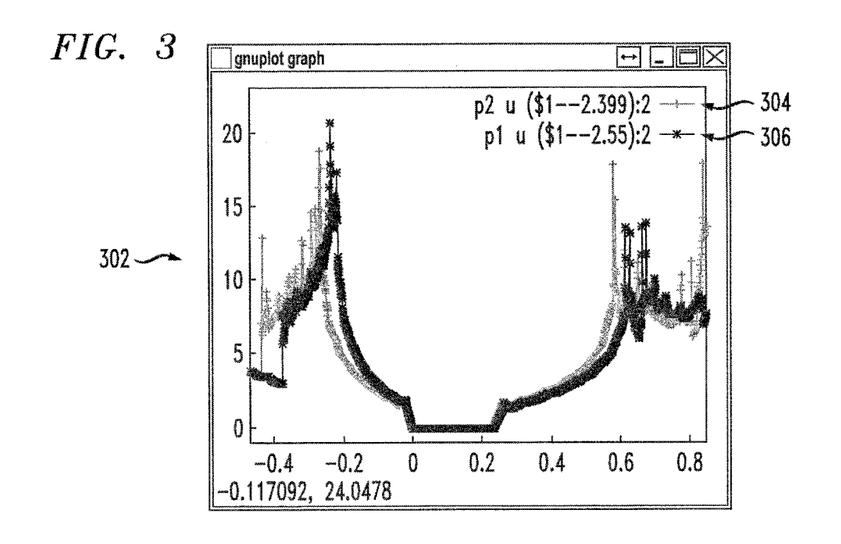
FIG. 3 is a graph illustrating density of states (DOS) for the nanomeshes depicted in FIG. 1 and FIG. 2, according to an embodiment of the present invention.

FIG. 3 is a graph 302 illustrating density of states (DOS) for the nanomeshes depicted in FIG. 1 and FIG. 2, according to an embodiment of the present invention. By way of illustration, FIG. 3 depicts the DOS of the systems in FIG. 1 (line 304) and FIG. 2 (line 306). The Fermi level is in the middle of the gap in both cases. The calculated DOS shows that the GNM electronic spectrum is not significantly changed by the receptor molecule (boronic acid). Also, the gap size as well as the Fermi level does not change due to the binding between the receptor and the GNM.

By way of illustration, the system in accordance with an embodiment of the invention is depicted in FIG. 1 and FIG. 2. As detailed herein, an aspect of the invention includes creating the GNMs with a hole size and hole lattice constant that is appropriate to the receptor used for detection. The GNMs are passivated such that the receptor can bind to the GNM. This can be achieved, for example, by creating the GNMs in air, water-vapor, ammonia or other environments. As illustrated, FIG. 1 depicts a water-vapor passivated GNM. The receptor binds to the GNM, providing the structure shown in FIG. 2.

For illustration purposes, consider two cases in the following example: one case for a semiconducting GNM (gap ~0.3 electron volt (eV)), and the second for a GNM with a larger hole lattice constant (gap ~0.1 eV). The size of the GNM gap depends on the geometrical details of the hole lattice. GNMs can also be semi-metallic like graphene (zero gap but a vanishing DOS at the Fermi energy). In any event, the Fermi level will always be in a zero DOS point, giving a relatively high GNM sheet resistance. In FIG. 3, the DOS of the passivated GNM is depicted before (curve 304) and after (curve 306) the binding with the GNM. As illustrated, there is no significant change on the electronic spectrum of the system due to the binding of the boronic acid receptor. This can be a general behavior of receptors used for various target molecules so that the sheet conductance of the GNM-receptor complex is not perturbed by the binding of the receptor.

Figure 4:
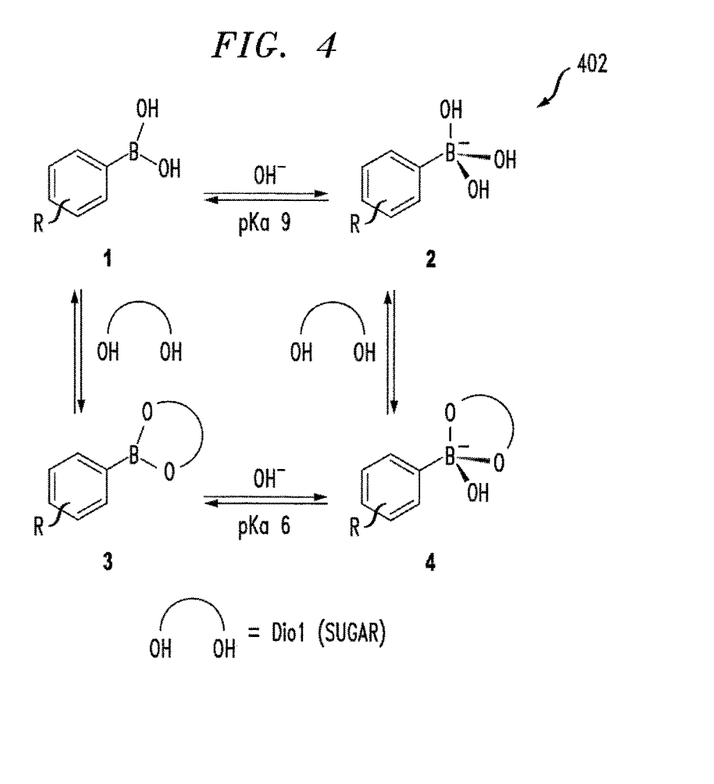
FIG. 4 is a diagram illustrating the chemical scheme for the reaction of glucose with a boronic-acid functionalized graphene nanomesh, according to an embodiment of the present invention.
Figure 5:
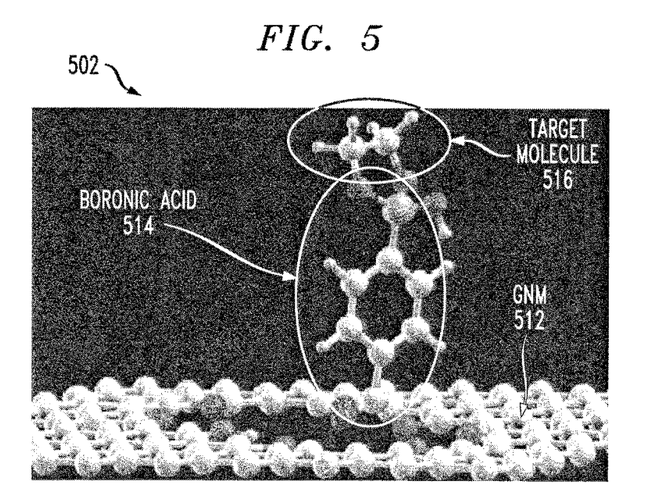
FIG. 5 is a diagram illustrating a post-glucose reaction graphene nanomesh structure including the extra OH— group attached to the boronic acid, according to an embodiment of the present invention.

FIG. 4 is a diagram illustrating the chemical scheme 402 for the reaction of glucose with a boronic-acid functionalized graphene nanomesh, according to an embodiment of the present invention. In this reaction, a boronic acid functional group reacts with two hydroxyl group of the sugar (vicinal diols) to form a cyclic ether with a net negative charge on boron, as depicted in compound 4 in FIG. 4. FIG. 5 is a diagram illustrating a post-glucose reaction graphene nanomesh structure 502 including the extra OH— group attached to the boronic acid, according to an embodiment of the present invention. Additionally, FIG. 5 depicts the GNM 512, the boronic acid 514 and the target molecule 516.

By way of illustration, FIG. 4 and FIG. 5 depict reaction results in the compound according to an embodiment of the invention. A comparison is provided herein of the electronic properties of the system before and after the reaction with glucose, taking into consideration the extra charge that the OH compound brings to the receptor. Calculations indicate that this extra charge is partially donated to the Pi-cloud of the GNM, moving the Fermi level to a higher DOS region which would be observed as a boost in the sheet conductance.

Figure 6:
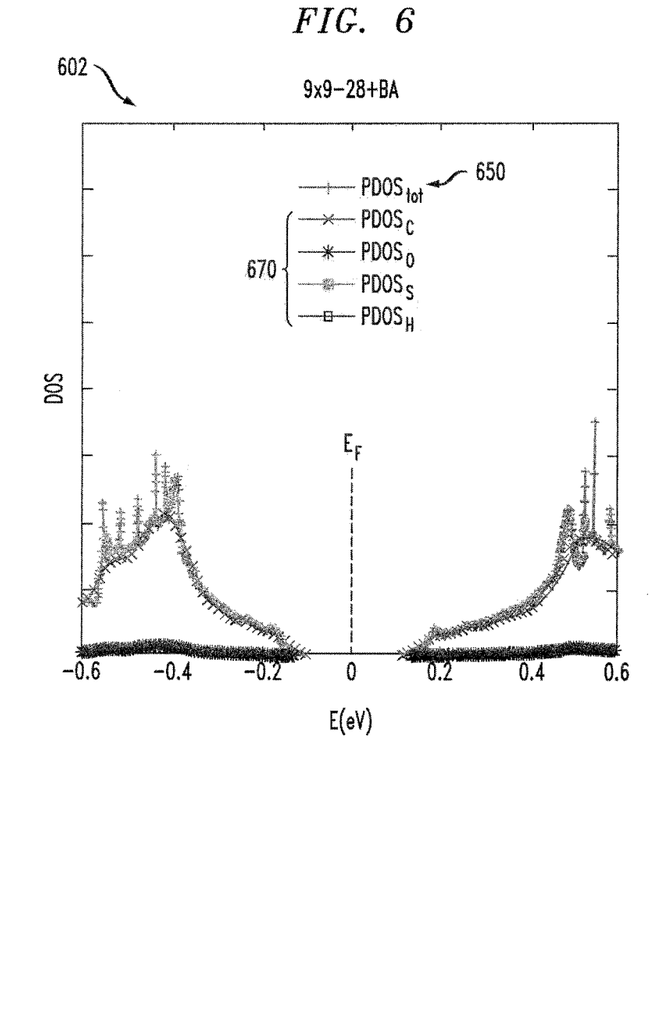
FIG. 6 is a graph illustrating density of states (DOS) and projected density of states (PDOS) for a functionalized 9×9 super-cell graphene nanomesh before reaction with a glycol group, according to an embodiment of the present invention.
Figure 7:
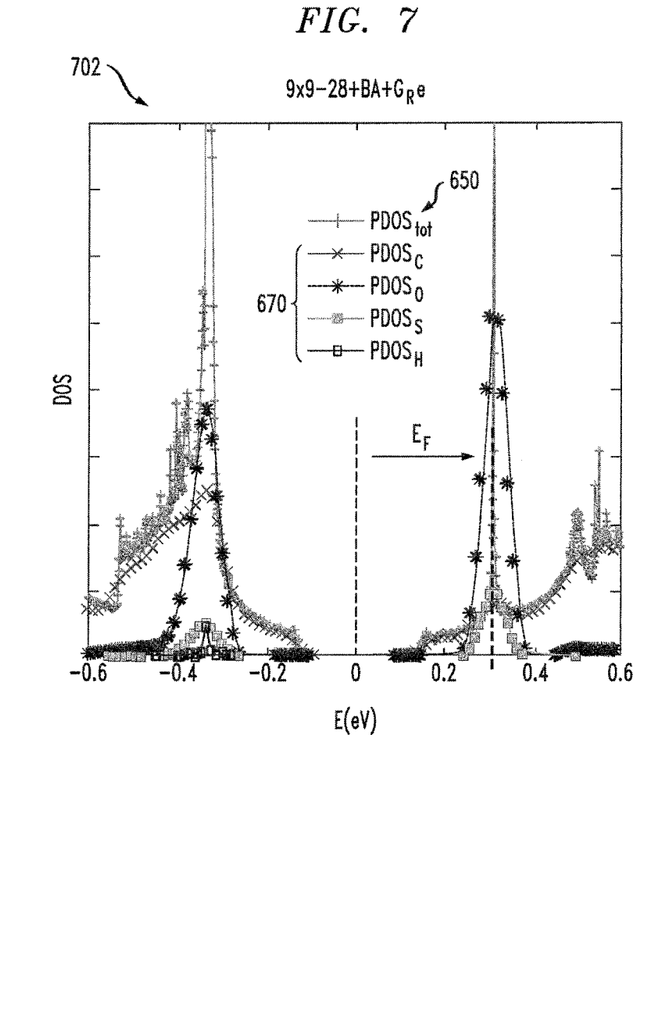
FIG. 7 is a graph illustrating density of states (DOS) and projected density of states (PDOS) for a functionalized 9×9 super-cell graphene nanomesh after reaction with a glycol group, according to an embodiment of the present invention.

FIG. 6 is a graph 602 illustrating density of states (DOS) and projected density of states (PDOS) for a functionalized 9×9 super-cell graphene nanomesh before reaction with a glycol group, according to an embodiment of the present invention. FIG. 7 is a graph 702 illustrating density of states (DOS) and projected density of states (PDOS) for a functionalized 9×9 super-cell graphene nanomesh after reaction with a glycol group, according to an embodiment of the present invention.

By way of illustration, FIG. 6 and FIG. 7 depict the total DOS (curve 650) of the passivated GNM after the functionalization with boronic acid, as well as the projected density of states (PDOS) (curves identified as 670) showing the contribution of various atomic species. The reaction with the glycol group adds the negatively charged OH group that attaches to the boron. This negative charge lives partially in the graphene sheet states, thereby shifting the Fermi level away from the gap. Also, the graphene-like spectrum remains persistent.

Figure 8:
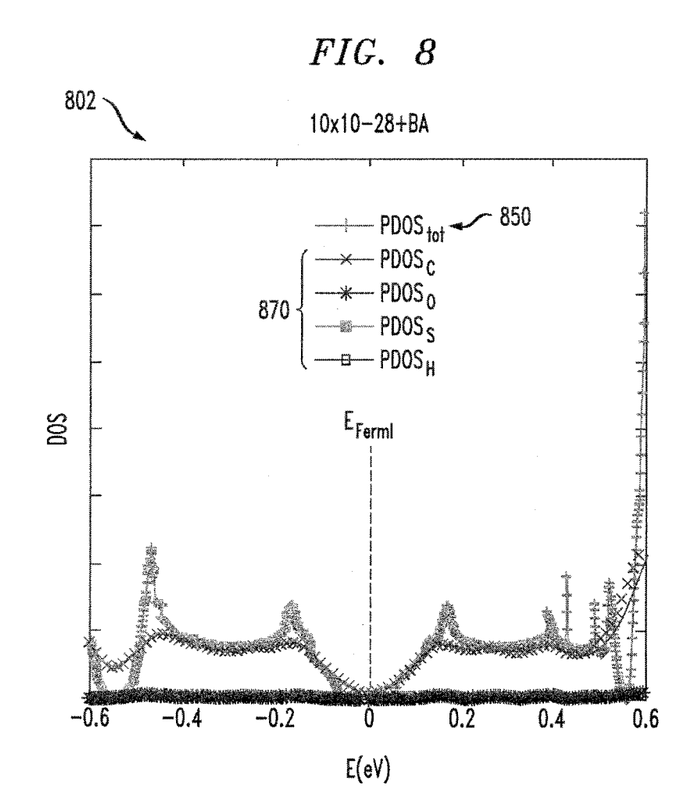
FIG. 8 is a graph illustrating density of states (DOS) and projected density of states (PDOS) for a functionalized 10×10 super-cell graphene nanomesh before reaction with a glycol group, according to an embodiment of the present invention.
Figure 9:
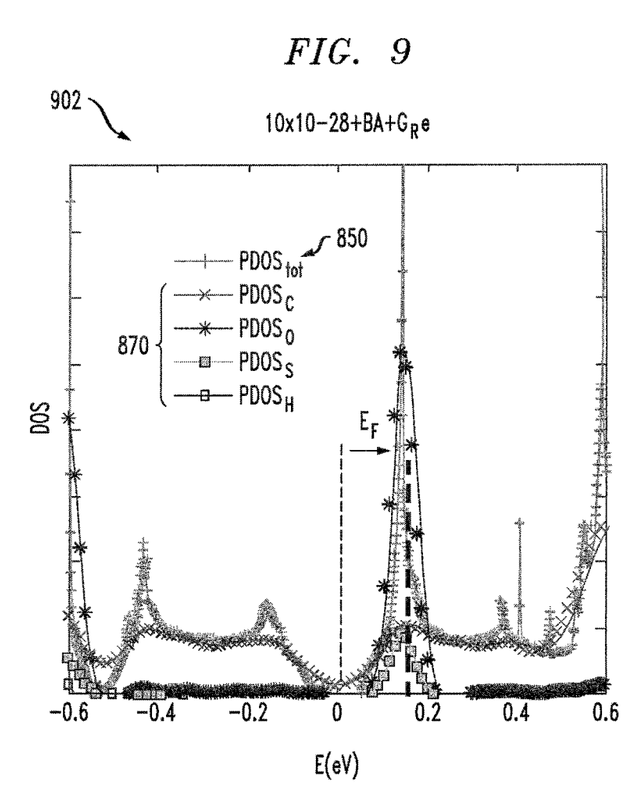
FIG. 9 is a graph illustrating density of states (DOS) and projected density of states (PDOS) for a functionalized 10×10 super-cell graphene nanomesh after reaction with a glycol group, according to an embodiment of the present invention.

FIG. 8 is a graph 802 illustrating density of states (DOS) and projected density of states (PDOS) for a functionalized 10×10 super-cell graphene nanomesh before reaction with a glycol group, according to an embodiment of the present invention. FIG. 9 is a graph 902 illustrating density of states (DOS) and projected density of states (PDOS) for a functionalized 10×10 super-cell graphene nanomesh after reaction with a glycol group, according to an embodiment of the present invention. By way of illustration, FIG. 8 and FIG. 9 depict the total DOS (curve 850) of the passivated GNM after the functionalization with boronic acid, as well as the projected density of states (PDOS) (curves identified as 870) showing the contribution of various atomic species.

Further, FIG. 8 and FIG. 9 depict similar results to those depicted in FIG. 6 and FIG. 7 for a GNM with a larger hole lattice constant. As described herein, varying the GNM parameters will define the width of the band gap of the GNM (ranging from zero for semi-metallic GNMs to a few tenths of an eV for semiconducting ones).

Using a Hirschfeld analysis of the systems, an aspect of the invention includes calculating the net electronic charges on various atoms. Hirschfeld analysis, as understood by one skilled in the art, is a method frequently used in computational chemistry for determining the atomic charges in a system. This allows for confirmation that a net charge was transferred to the GNM. For the first hole lattice configuration considered, for example, in FIG. 6 and FIG. 7 (9×9 super-cell), there is shown a net charge of 0.38 electrons transferred to the sheet. For the larger hole lattice, for example, as considered in FIG. 8 and FIG. 9 (10×10 super-cell), the charge transferred is 0.42 electrons.

Figure 10:
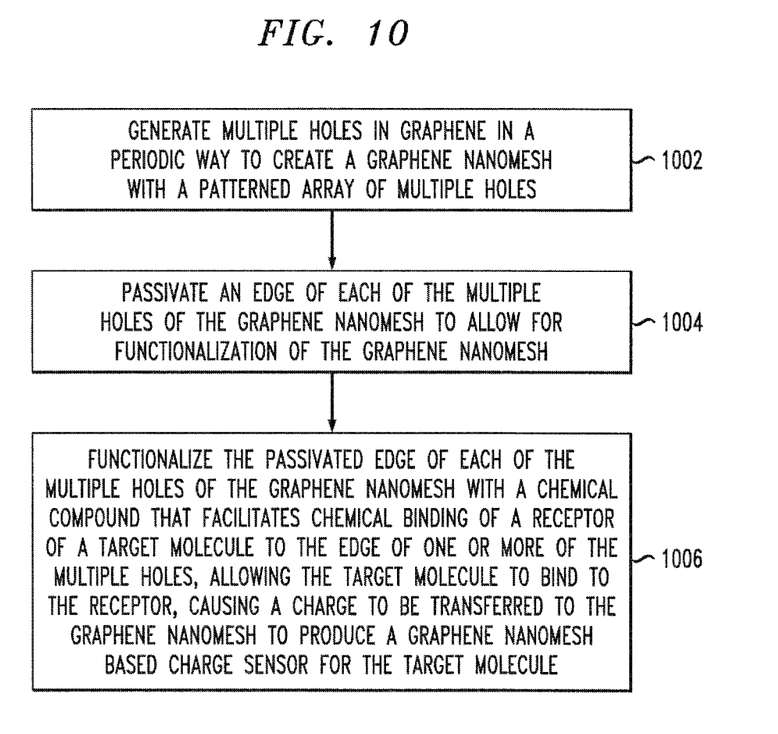
FIG. 10 is a flow diagram illustrating techniques for producing a graphene nanomesh based charge sensor, according to an embodiment of the present invention.

FIG. 10 is a flow diagram illustrating techniques for producing a graphene nanomesh based charge sensor, according to an embodiment of the present invention. Step 1002 includes generating multiple holes in graphene in a periodic way to create a graphene nanomesh with a patterned array of multiple holes. Generating multiple holes in graphene in a periodic way to create a graphene nanomesh with a patterned array of multiple holes includes generating holes in graphene in a periodic way to create a graphene nanomesh with a patterned array of holes in terms of hole size and hole lattice. In an example embodiment, each hole has a size in a range of approximately 5 nanometers to approximately 20 nanometers, and the patterned array of multiple holes has a pitch in a range of approximately 3× to approximately 6×.

Step 1004 includes passivating an edge of each of the multiple holes of the graphene nanomesh to allow for functionalization of the graphene nanomesh. As described herein, upon passivation, the GNM hole edges are passivated with chemical groups (such as OH or NH2) that can be used for functionalization.

Step 1006 includes functionalizing the passivated edge of each of the multiple holes of the graphene nanomesh with a chemical compound that facilitates chemical binding of a receptor of a target molecule to the edge of one or more of the multiple holes, allowing the target molecule to bind to the receptor, causing a charge to be transferred to the graphene nanomesh to produce a graphene nanomesh based charge sensor for the target molecule. Functionalizing the passivated edge of each of the multiple holes of the graphene nanomesh with a chemical compound that facilitates chemical binding of a receptor of a target molecule to the edge of one or more of the multiple holes increases conductance of the graphene nanomesh.

If the GNM is exposed to atmosphere immediately after drilling the hole, edges are passivated by reaction with oxygen or water molecules and form a hydroxyl group either as a phenol or an alcohol functional group. The phenolic or alcoholic functional group can be reacted with carboxy-containing compounds to form ester linkage. For example, if the group is reacted with 4-carboxylphenylboronic acid, boronic acid esters covalently bonded to the graphene nanomesh are formed.

As detailed herein, each of the multiple holes of the graphene nanomesh can be a size appropriate to bind with a receptor of a target molecule. In at least one embodiment of the invention, the receptor is a molecule that reacts with the graphene nanomesh (for example, binds to the edges of the GNM) yielding a functionalized graphene nanomesh. Additionally, the receptor is a molecule that chemically binds to the target molecule, irrespective of the size of the target molecule.

The techniques depicted in FIG. 10 also include controlling density of a receptor sites by controlling at least one characteristic of the patterned array of multiple holes of the graphene nanomesh such as, for example, hole size and lattice constant. By controlling the number of holes made per unit area of the GNM, as well as the size of the holes, the number of receptor sites per unit area can be controlled.

An aspect of the invention also includes a graphene nanomesh based charge sensor (produced according to the techniques described herein), which includes a graphene nanomesh with a patterned array of multiple holes created by generating multiple holes in graphene in a periodic way, wherein an edge of each of the multiple holes of the graphene nanomesh is passivated, and the passivated edge of each of the multiple holes of the graphene nanomesh is functionalized with a chemical compound that facilitates chemical binding of a receptor of a target molecule to the edge of one or more of the multiple holes, allowing the target molecule to bind to the receptor, causing a charge to be transferred to the graphene nanomesh to produce a graphene nanomesh based charge sensor for the target molecule.

As detailed herein, the receptor is bound to the edge of the hole. Once the target molecule (for example, glucose) approaches the receptor (for example, boronic acid), the target molecule (or a portion thereof) binds to the receptor. As a result, a charge transfer occurs. Part of that charge reaches the underlying GNM, causing a boost in the conductance of the GNM.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A graphene nanomesh charge based sensor for the detection of glucose comprising: a graphene nanomesh comprising;
   (a) a periodic patterned array of multiple holes, wherein the periodic patterned array of multiple holes is periodic in terms of lattice size and lattice constant, and wherein each hole of multiple holes in the periodic patterned array comprises:
      (i) a hole size in the range of approximately 5 nanometers to approximately 20 nanometers;
      (ii) a hole lattice constant gap ranging from approximately 0.1 electron volt to approximately 0.3 electron volt;
      (iii) a pitch range of approximately 3× to approximately 6×;
      (iv) a passivated edge functionalized with a functional group selected from the group consisting of: O, H, OH, and $NH_2$, wherein the functional group facilitates chemical binding of a 4-carboxyphenylboronic acid molecule to the passivated edge of one or more holes of the multiple holes in the periodic patterned array of the graphene nanomesh; and
      (v) at least one 4-carobxyphenylboronic acid molecule bound through the 4-carboxy functionality of the 4-carobxylphenylboronic acid molecule to the functional group of the passivated edge of one or more of the multiple holes in the periodic patterned array of the graphene nanomesh to form at least one 4-carboxyphenylboronic acid ester linkage to the functional group of the passivated edge; and
      (vi) at least one glucose molecule bound to each of the at least one 4-carboxyphenylboronic acid esters through a vicinal diol group of the at least one glucose molecule to form a cyclic ether, wherein a net charge is transferred to the graphene nanomesh, thereby n-doping the graphene nanomesh and producing a graphene nanomesh based charge sensor for at least one glucose molecule;
   (b) a specific charge, wherein the specific charge is based on the at least one glucose molecule bound to the at least one 4-carobxyphenylboronic acid molecule; and
   (c) a specific resistance sensitivity, wherein the specific resistance sensitivity is based on the specific charge.

2. The graphene nanomesh charge based sensor for the detection of glucose of claim 1, wherein the pitch is 4×.

3. The graphene nanomesh charge based sensor for the detection of glucose of claim 1, wherein the functional group is OH.

4. The graphene nanomesh charge based sensor for the detection of glucose of claim 1, wherein the functional group is $NH_2$.

5. The graphene nanomesh charge based sensor for the detection of glucose of claim 1, wherein the specific charge is between 0.1 electron and 1 electron transferred to the graphene nanomesh.

* * * * *